(12) United States Patent
Kwon

(10) Patent No.: US 10,624,688 B2
(45) Date of Patent: Apr. 21, 2020

(54) CANNULATED SCREW

(71) Applicant: INJE UNIVERSITY INDUSTRY-ACADEMIC COOPERATION FOUNDATION, Gimhae-si, Gyeongsangnam-do (KR)

(72) Inventor: Yonguk Kwon, Busan (KR)

(73) Assignee: INJE UNIVERSITY INDUSTRY-ACADEMIC COOPERATION FOUNDATION, Gimhae-si, Gyeongsangnam-do (KR)

(*) Notice: Subject to any disclaimer, the term of this patent is extended or adjusted under 35 U.S.C. 154(b) by 62 days.

(21) Appl. No.: 16/066,671

(22) PCT Filed: Jul. 22, 2016

(86) PCT No.: PCT/KR2016/008007
§ 371 (c)(1),
(2) Date: Jun. 28, 2018

(87) PCT Pub. No.: WO2017/146319
PCT Pub. Date: Aug. 31, 2017

(65) Prior Publication Data
US 2019/0021775 A1 Jan. 24, 2019

(30) Foreign Application Priority Data
Feb. 26, 2016 (KR) .................. 10-2016-0023207

(51) Int. Cl.
*A61B 17/04* (2006.01)
*A61B 17/86* (2006.01)
*A61F 2/08* (2006.01)
*A61B 17/88* (2006.01)

(52) U.S. Cl.
CPC ............ *A61B 17/864* (2013.01); *A61B 17/86* (2013.01); *A61B 17/8605* (2013.01); *A61B 17/88* (2013.01); *A61B 17/8897* (2013.01); *A61B 17/8695* (2013.01)

(58) Field of Classification Search
CPC combination set(s) only.
See application file for complete search history.

(56) References Cited

U.S. PATENT DOCUMENTS 6,030,162 A 2/2000 Huebner
7,325,470 B2 2/2008 Kay et al.
(Continued)

FOREIGN PATENT DOCUMENTS

KR 20-0383131 Y1 4/2005

OTHER PUBLICATIONS

International Search Report for PCT/KR2016/008007 dated Oct. 21, 2016 from Korean Intellectual Property Office.

*Primary Examiner* — Sameh R Boles
(74) *Attorney, Agent, or Firm* — Revolution IP, PLLC

(57) ABSTRACT

A cannulated screw includes: a body portion that comprises a screw thread formed by protruding along an outer surface and has a through-hole at a center of the body portion; and a head portion that has one side surface combined to one end of the body portion, another side surface formed in a curved surface in which a center portion has a concave shape, and a connection hole communicating with the through-hole at a center of the head portion.

3 Claims, 3 Drawing Sheets

(56) References Cited

U.S. PATENT DOCUMENTS

| | | |
|---|---|---|
| 8,197,517 B1 * | 6/2012 | Lab .................... A61B 17/7037 606/268 |
| 8,529,609 B2 | 9/2013 | Helgerson et al. |
| 8,721,694 B2 | 5/2014 | Patterson et al. |
| 2006/0293677 A1 | 12/2006 | Oepen |

* cited by examiner

CANNULATED SCREW

TECHNICAL FIELD

The present disclosure relates to a cannulated screw, and more particularly, to a cannulated screw having a hole penetrating therethrough to be inserted into a bone.

BACKGROUND ART

Generally, a cannulated screw is used to be inserted into a fractured bone, fixed to the bone, and then removed after a certain period of time. Such a cannulated screw has a hole penetrating a center portion, and when used for a fractured region that is difficult to be identified with naked eyes, a guide wire may be inserted into the hole. In other words, the guide wire is pre-installed at the fractured region, the guide wire is penetrated through the hole of the cannulated screw, and then the cannulated screw is moved along the guide wire and fixed to the fractured region. On the other hand, when the cannulated screw is to be removed, the guide wire is inserted into the hole of the cannulated screw at a location where the cannulated screw is fixed, and then the cannulated screw is removed along the guide wire.

Technology about a conventional cannulated screw as described above is disclosed in Korean Registered Utility Model No. 20-0383131.

However, according to the conventional cannulated screw, when the cannulated screw inserted into the fractured region is removed, the guide wire needs to be accurately located and inserted into the hole of the cannulated screw. However, it is difficult to accurately insert the guide wire into the hole, i.e., the center portion, because it is difficult to identify the fractured region with naked eyes, and there is inconvenience that a location of the guide wire needs to be indirectly checked by using an apparatus, such as a C-arm during insertion. Also, when the inserted guide wire deviates from the center portion of the cannulated screw, it is difficult to insert the guide wire into the hole, and thus the guide wire needs to be inserted again.

DESCRIPTION OF EMBODIMENT

Technical Problem

Provided is a cannulated screw that is easily removed from a fractured region because a hole of the cannulated screw is easily found even when a location of a guide wire deviates from a center portion.

Solution to Problem

According to an aspect of the present disclosure, a cannulated screw includes: a body portion that includes a screw thread formed by protruding along an outer surface and has a through-hole at a center of the body portion; and a head portion that has one side surface combined to one end of the body portion, another side surface formed in a curved surface in which a center portion has a concave shape, and a connection hole communicating with the through-hole at a center of the head portion.

The cannulated screw may further include a washer that has an insertion hole into which the head portion is inserted at a center of the washer, includes, at one side surface, an accommodating portion where the head portion is accommodated by being formed to protrude along an inner surface of the insertion hole, and has another side surface formed in a curved surface in which a center portion has a concave shape.

An inner diameter of the accommodating portion may be formed to be smaller than an outer diameter of the head portion such that the one side surface of the head portion contacts one side surface of the accommodating portion.

The other side surface of the washer may be provided at a location protruding farther than the other side surface of the head portion.

Advantageous Effects of Disclosure

According to a cannulated screw of the present disclosure, a shape of a head portion contacting a guide wire has a curved surface, in which a center portion is concave, to guide the guide wire to be located at the center, and thus a connection hole of a cannulated screw can be easily found.

Also, a washer having a curved surface, in which a center portion is concave, is further provided to guide the guide wire to be located at the center even in a range wider than the head portion, and thus the guide wire can be easily inserted into the connection hole. Accordingly, the cannulated screw can be quickly and safely removed.

BEST MODE

Hereinafter, embodiments of the present disclosure will be described with reference to accompanying drawings. The terms or words used herein must not be interpreted in their common or dictionary definitions, but must be interpreted in the meanings and concept corresponding to the aspect of the present disclosure, based on the principle that the inventor(s) can suitably define the concept of terms in order to describe the disclosure in the best manner.

Accordingly, the embodiments and drawings described herein are only preferred examples, and do not represent the technical aspects of the present disclosure. Thus, one of ordinary skill in the art understands that the disclosure may be embodied in many different forms.

Hereinafter, embodiments of the present disclosure are described in detail with reference to accompanying drawings.

Figure 1:
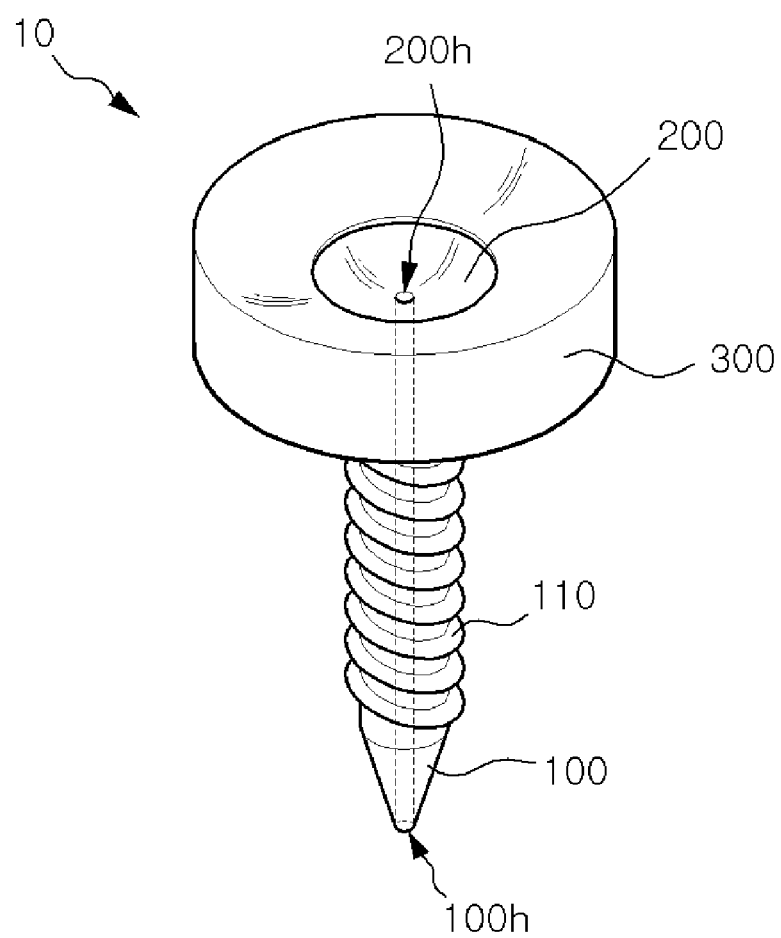
FIG. 1 is a perspective view of a cannulated screw according to an embodiment of the present disclosure.
Figure 2:
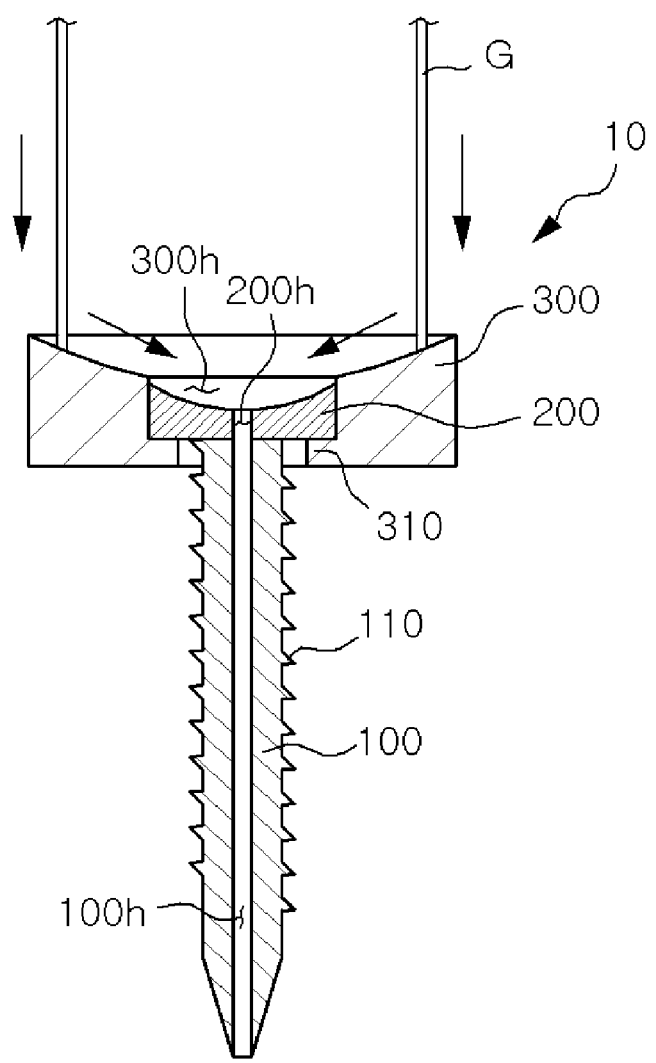
FIG. 2 is a cross-sectional view of the cannulated screw of FIG. 1.
Figure 3:
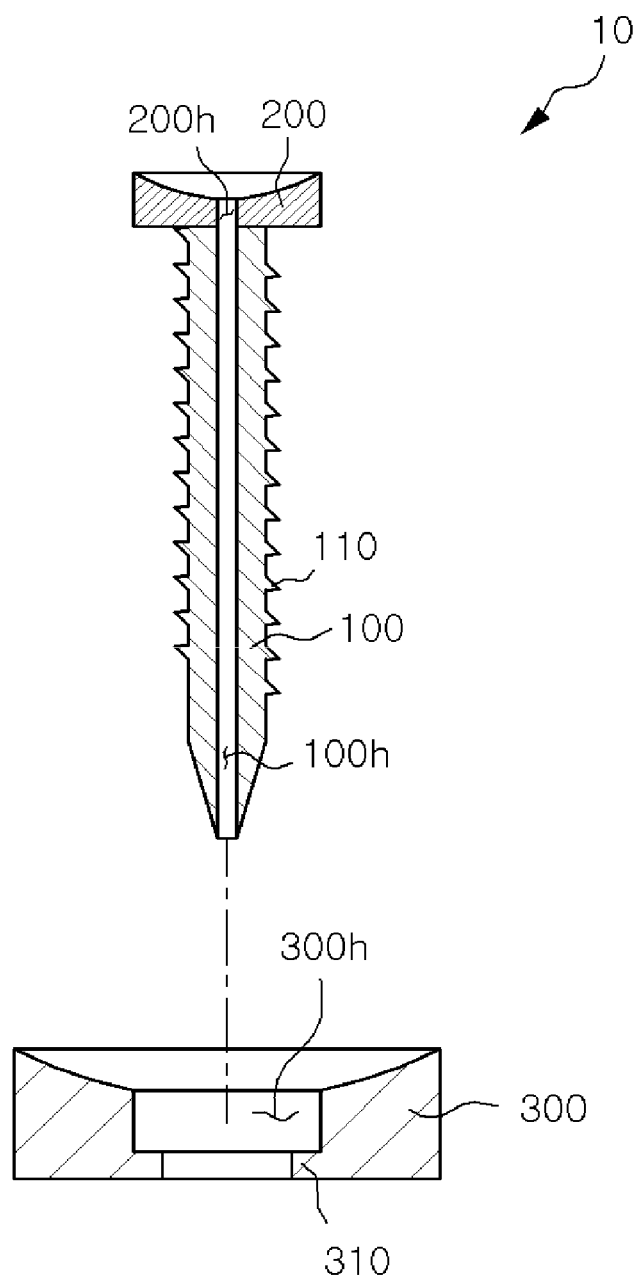
FIG. 3 is an exploded cross-sectional view in which a washer and a head portion of the cannulated screw of FIG. 1 are disassembled.

Referring to FIGS. 1 through 3, a cannulated screw 10 according to an embodiment of the present disclosure includes a body portion 100 and a head portion 200. Also, the cannulated screw 10 may further include a washer 300. The cannulated screw 10 may be rotated by using a tool, such as a screw driver or a wrench, and may be inserted into a fractured region by being rotated.

The body portion 100 may have a cylindrical shape, and includes a screw thread 110 on an outer surface thereof. The screw thread 110 may be formed by protruding along an outer surface of the cylindrical shape, and formed in a spiral shape. The screw thread 110 is rotated while contacting the fractured region to be inserted into the fractured region and, before fixing the cannulated screw 10 to the fractured region, a hole may be made in the fractured region by using drilling and tapping operations, and then the body portion 100 may be positioned at the hole such that the screw thread 110 contacts and is fixed to an inner surface of the hole.

The body portion 100 includes a through-hole 100h at the center. A guide wire G is inserted into the through-hole 100h, and the body portion 100 may be moved towards or deviated from the fractured region according to a guide of the guide wire G.

One side surface of the head portion 200 is combined to one end of the body portion 100. Also, the other side surface of the head portion 200 has a curved surface in which a center portion has a concave shape. The head portion 200 includes a connection hole 200h at the center, the connection hole 200h communicating with the through-hole 100h. In other words, a passage may be formed at the inner center of the cannulated screw 10 as the connection hole 200h and the through-hole 100h are connected to each other and penetrate the cannulated screw 10, and the guide wire G may be inserted into the connection hole 200h and the through-hole 100h.

Since the other side surface of the head portion 200 has the curved surface in which the center portion has the concave shape, the guide wire G may be accurately and quickly moved to the connection hole 200h even when the guide wire G contacts the other side surface of the head portion 200, i.e., a location deviated from the connection hole 200h. In other words, when slight force is applied after the guide wire G contacts the head portion 200, the guide wire G is guided towards the connection hole 200h formed at the center of the head portion 200, along the curved surface of the head portion 200, in which the center portion is concave. Accordingly, the guide wire G is accurately and quickly moved to the connection hole 200h, and thus the connection hole 200h of the cannulated screw 10 fixed at the fractured region that is unable to be identified with naked eyes is easily found. Since the cannulated screw 10 is easily removed by quickly finding the connection hole 200h, stability is increased.

The washer 300 is provided such that the head portion 200 is inserted thereto and the head portion 200 and the body portion 100 are fixed to a proper location of the fractured region. In other words, the washer 300 is combined to the head portion 200 to increase structural stability and increase a coupling effect when the cannulated screw 10 is coupled to the fractured region. The washer 300 includes an insertion hole 300h at the center, into which the head portion 200 is inserted. In other words, the insertion hole 300h may have a size corresponding to that of the head portion 200. Also, the washer 300 may include an accommodating portion 310.

The accommodating portion 310 is where the head portion 200 is accommodated after being inserted into the insertion hole 300h, and is formed to protrude along an inner surface of the insertion hole 300h. In other words, the head portion 200 is accommodated at one surface of the accommodating portion 310. An inner diameter of the accommodating portion 310 may be smaller than an outer diameter of the head portion 200 such that one side surface of the head portion 200 contacts and accommodates at one side surface of the accommodating portion 310.

Also, another side surface of the washer 300 may have a curved surface in which a center portion has a concave shape. By forming the center portion of the other side surface of the washer 300 in a concave shape, when slight force is applied after the guide wire G contacts the other side surface of the washer 300, the guide wire G is easily moved towards the connection hole 200h by moving to the head portion 200 inserted into the insertion hole 300h, along the curved surface of the washer 300, in which the center portion is concave. Accordingly, the guide wire G may be accurately and quickly moved to the connection hole 200h even in a range wider than the head portion 200. The cannulated screw 10 inserted into a bone is easily removed because the guide wire G is accurately and quickly moved to the connection hole 200h. Further, the other side surface of the washer 300 may be provided at a location protruding farther than the other side surface of the head portion 200. In other words, the guide wire G is easily moved to the connection hole 200h without being interrupted at a boundary between the washer 300 and the head portion 200.

According to the cannulated screw 10 described above, a shape of the head portion 200 contacting the guide wire G has a curved surface, in which a center portion is concave, to guide the guide wire G to be located at the center, and thus the connection hole 200h may be easily found.

Also, the washer 300 having the curved surface, in which the center portion is concave, is provided to guide the guide wire G to be located at the center even in a range wider than the head portion 200, and thus the guide wire G may be easily inserted into the connection hole 200h.

Accordingly, the cannulated screw 100 may be quickly and safely removed.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

| = Explanation of Reference Numerals = | |
|---|---|
| 10: Cannulated Screw | 100: Body Portion |
| 100h: Through-Hole | 110: Screw Thread |
| 200: Head Portion | 200h: Connection Hole |
| 300: Washer | 300h: Insertion Hole |
| 310: Accommodating Portion | G: Guide Wire |

The invention claimed is:

1. A cannulated screw comprising:
    a body portion that comprises a screw thread formed by protruding along an outer surface and has a through-hole at a center of the body portion;
    a head portion that has one side surface combined to one end of the body portion, another side surface formed in a curved surface in which a center portion has a concave shape, and a connection hole communicating with the through-hole at a center of the head portion; and
    a washer comprising an opening portion, in insertion hole, and an accommodating portion,
        the opening portion having a depth that has a top portion and a bottom portion, wherein a diameter the top portion gradually reduces towards to the bottom portion, a diameter of the top portion being same as a diameter of the washer, a diameter of the bottom portion being same as a diameter of the insertion hole,
        the insertion hole into which the head portion is inserted at a center of the washer,
        at one side surface of the washer, the accommodating portion where the head portion is accommodated by being formed to protrude along an inner surface of the insertion hole, and the washer having a curved top surface in which a center portion has a concave shape.

2. The cannulated screw of claim 1, wherein an inner diameter of the accommodating portion is formed to be smaller than an outer diameter of the head portion such that the one side surface of the head portion contacts one side surface of the accommodating portion.

3. The cannulated screw of claim 1, wherein the other side surface of the washer is provided at a location protruding farther than the other side surface of the head portion.

* * * * *